United States Patent
Ohuchida et al.

(10) Patent No.: US 6,288,119 B1
(45) Date of Patent: Sep. 11, 2001

(54) 11,15-O-DIALKYLPROSTAGLANDIN E DERIVATIVES, PROCESS FOR PRODUCING THE SAME, AND DRUGS CONTAINING THE SAME AS THE ACTIVE INGREDIENT

(75) Inventors: Shuichi Ohuchida; Takayuki Maruyama, both of Osaka (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/355,626

(22) PCT Filed: Feb. 10, 1998

(86) PCT No.: PCT/JP98/00544

§ 371 Date: Aug. 2, 1999

§ 102(e) Date: Aug. 2, 1999

(87) PCT Pub. No.: WO98/34916

PCT Pub. Date: Aug. 13, 1998

(30) Foreign Application Priority Data

Feb. 10, 1997 (JP) .................................... 9-041571

(51) Int. Cl.[7] ........................ A61K 31/5575; C07C 61/20
(52) U.S. Cl. ............................. 514/573; 562/503
(58) Field of Search ............................. 562/503; 514/573

(56) References Cited

U.S. PATENT DOCUMENTS 3,835,180 * 9/1974 Lincoln, Jr. .
5,004,752 * 4/1991 Raduechel et al. .
5,091,417 * 2/1992 Watanabe et al. .

OTHER PUBLICATIONS

Ohno, K., et al "A mild methylation of alcohols with diazomethane catalyzed by silical gel" Tet. Lett. No. 45 pp 4405–4406, 1979.*

* cited by examiner

Primary Examiner—Gary Geist
Assistant Examiner—Leigh C. Maier
(74) Attorney, Agent, or Firm—Stevens, Davis, Miller & Mosher, L.L.P.

(57) ABSTRACT

The present invention provides 11,15-O-dialkyl prostaglandin E derivatives of formula (I)

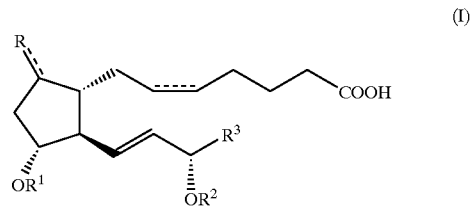

(wherein all symbols are as described in Specification), or non-toxic salts thereof or cyclodextrin clathrates thereof, processes for the preparation thereof and pharmaceutical compositions containing them as active ingredient.

A compound of formula (I) binds strongly and acts on $EP_3$ receptor which is a subtype of $PGE_2$ receptor and therefore is useful for prevention and/or treatment of liver diseases, kidney diseases, pancreatitis, myocardial infarction etc.

14 Claims, No Drawings

11,15-O-DIALKYLPROSTAGLANDIN E DERIVATIVES, PROCESS FOR PRODUCING THE SAME, AND DRUGS CONTAINING THE SAME AS THE ACTIVE INGREDIENT

TECHNICAL FIELD

The present invention relates to 11,15-O-dialkyl prostaglandin E derivatives. More particularly, this invention relates to
(1) 11,15-O-dialkyl prostaglandin E derivatives of formula (I)

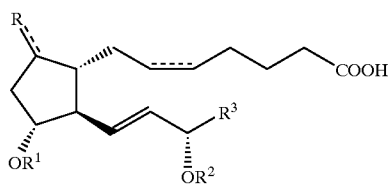

(wherein all symbols are as defined hereinafter), non-toxic salts thereof and cyclodextrin clathrates thereof,
(2) processes for the preparation thereof and
(3) pharmaceutical compositions containing them as active ingredient.

BACKGROUND

Prostaglandin $E_2$ (abbreviated as $PGE_2$ hereinafter) has been known as a metabolite in the arachidonic acid cascade. It has been known that $PGE_2$ has cyto-protective activity, uterine contractile activity, a pain-inducing effect, a promoting effect on digestive peristalsis, an awakening effect, a suppressive effect on gastric acid secretion, hypotensive activity and diuretic activity etc.

In the recent studies, it was found that the $PGE_2$ receptor was divided into some subtypes which possess different roles from each other. At present, four main receptor subtypes are known and they are called $EP_1$, $EP_2$, $EP_3$ and $EP_4$, respectively (Negishi M. et al., J. Lipid Mediators Cell Signaling 12, 379–391 (1995)).

$PGE_2$ has various kinds of physiological activities, and so it has the disadvantage that its undesired effect leads to a side effect. Research to overcome this disadvantage has been carried on by investigating the roles of each subtype and obtaining those compounds which are effective only on the subtype.

Accordingly, the present inventors investigated to find those compounds which bind on $EP_3$ subtype receptor specifically, so that we found that 11,15-O-dialkyl prostaglandin E derivatives of formula (I) could bind specifically on $EP_3$ receptor and hardly on other subtype receptors, and we achieved the present invention.

As to the compounds whose structures are similar to those of the compounds of the present invention of formula (I), the following techniques are known.

In JP55-115836, processes for the preparation of methyl ether derivatives are disclosed, wherein 11,15-O-dimethyl-prosta-5Z,13E-dienoic acid methyl ester is synthesized from prostaglandin $E_2$, but nothing is described about the utility of the compounds obtained.

In JP47-42647, it is described that 15-O-alkyl ether prostaglandin E derivatives have PG-like activity. More particularly, 15-O-methyl-$PGE_2$ is described.

DISCLOSURE OF THE INVENTION

The present invention relates to
1) 11,15-O-dialkyl prostaglandin E derivatives of formula (I)

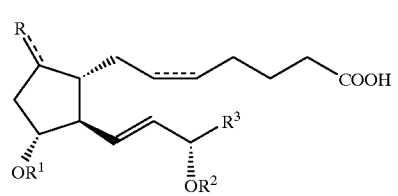

(wherein R is oxo or halogen atom,
$R^1$ and $R^2$ are each independently C1–4 alkyl,
$R^3$ is C1–10 alkyl, C2–10 alkenylene, C2–10 alkynylene, or C1–10 alkyl, C2–10 alkenyl or C2–10 akkeynyl substituted by phenyl, phenoxy, C3–7 cycloalkyl or C3–7 cycloalkyloxy, wherein phenyl and cycloalkyl may be substituted by 1–3 of C1–4 alkyl, C1–4 alkoxy, halogen, trihalomethyl or nitro, and === is bond or double-bond), or non-toxic salts thereof or cyclodextrin clathrates thereof,
2) processes for the preparation thereof and
3) pharmaceutical compositions containing them as active ingredient.

DESCRIPTION

In formula (I), C1–4 alkyl in the definitions of $R^1$, $R^2$ and $R^3$ means methyl, ethyl, propyl, butyl and isomers thereof.

In formula (I), C1–4 alkoxy in the definition of $R^3$ means methoxy, ethoxy, propoxy, butoxy and isomers thereof.

In formula (I), C1–10 alkyl in the definition of $R^3$ or represented by $R^3$ means methyl, ethyl, propyl, butyl, pentyl, hexyl, heptyl, octyl, nonyl, decyl and isomers thereof.

In formula (I), C2–10 alkenyl in the definition of $R^3$ or represented by $R^3$ means vinyl, propenyl, butenyl, pentenyl, hexenyl, heptenyl, octenyl, nonenyl, decenyl and isomers thereof.

In formula (I), C2–10 alkynyl in the definition of $R^3$ or represented by $R^3$ means ethynyl, propynyl, butynyl, pentynyl, hexynyl, heptynyl, octynyl, nonynyl, decynyl and isomers thereof.

In formula (I), C3–7 cycloalkyl in the definition of $R^3$ or represented by $R^3$ means cyclopropyl, cyclobutyl, cyclopentyl, cyclohexyl and cycloheptyl.

In formula (I), halogen in the definition of $R^3$ or represented by R means fluorine, chlorine, bromine and iodine.

In the present specification, as may be easily understood by those skilled in the art, unless otherwise specified, the symbol: ◂
indicates that the substituent attached thereto is in front of the sheet; unless otherwise specified, the symbol ⋯⋯
indicates that the substituent attached thereto is behind the sheet.

Unless otherwise specified, all isomers are included in the present invention. For example, alkyl, alkenyl and alkynyl groups include straight-chain and also branched-chain ones. Double-bond in alkenylene group includes E, Z and EZ mixed isomers. Isomers resulting from the presence of asymmetric carbon atom(s) e.g. in branched-chain alkyl are included in the present invention.

Preferred compounds among the present invention of formula (I) include compounds listed in the examples and the following.

(1) 11α,15α-dipropyloxy-9-oxoprosta-5Z,13E-dienoic acid,
(2) 11α,15α-dibutyloxy-9-oxoprosta-5Z,13E-dienoic acid,
(3) 11α-methoxy-15α-ethoxy-9-oxoprosta-5Z,13E-dienoic acid,
(4) 11α-methoxy-15α-propyloxy-9-oxoprosta-5Z,13E-dienoic acid,
(5) 11α-methoxy-15α-butyloxy-9-oxoprosta-5Z,13E-dienoic acid,
(6) 11α-ethoxy-15α-methoxy-9-oxoprosta-5Z,13E-dienoic acid,
(7) 11α-ethoxy-15α-propyloxy-9-oxoprosta-5Z,13E-dienoic acid,
(8) 11α-ethoxy-15α-butoxy-9-oxoprosta-5Z,13E-dienoic acid,
(9) 11α-propyloxy-15α-methoxy-9-oxoprosta-5Z,13E-dienoic acid,
(10) 11α-propyloxy-15α-ethoxy-9-oxoprosta-5Z,13E-dienoic acid,
(11) 11α-propyloxy-15α-butoxy-9-oxoprosta-5Z,13E-dienoic acid,
(12) 11α-butoxy-15α-methoxy-9-oxoprosta-5Z,13E-dienoic acid,
(13) 11α-butoxy-15α-ethoxy-9-oxoprosta-5Z,13E-dienoic acid,
(14) 11α-butoxy-15α-propyloxy-9-oxoprosta-5Z,13E-dienoic acid.

Salts

The compounds of the present invention of formula (I) may be converted into the corresponding salts by a conventional method. Non-toxic and water-soluble salts are preferable. Appropriate salts are described hereinafter; salts of alkali metals (e.g. potassium, sodium), salts of alkaline-earth metals (e.g. calcium, magnesium), ammonium salts, salts of pharmaceutically acceptable organic amines (tetramethyl ammonium, triethylamine, methylamine, dimethylamine, cyclopentylamine, benzylamine, phenethylamine, piperidine, monoethanolamine, diethanolamine, tris (hydroxymethyl)methylamine, lysine, arginine, N-methyl-D-glucamine etc.).

Cyclodextrin Clathrates 11,15-O-Dialkyl prostaglandin E derivatives of formula (I) may be converted into cyclodextrin clathrates using α-, β- or γ-cyclodextrin or their mixture, by the methods described in the specification of Japanese Kokoku No. 50-3362, Japanese Kokoku No.52-31404 or Japanese Kokoku No.61-52146. Conversion into their cyclodextrin clathrates serves to increase the stability and solubility in water of the compounds, and therefore it is convenient in the use for pharmaceuticals.

Processes for the Preparation of the Compounds of the Present Invention (1) A compound of the present invention of formula (I) may be prepared by subjecting to hydrolysis using an enzyme a compound of formula (II)

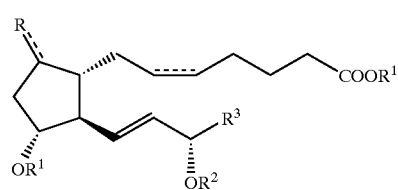

(wherein R, $R^1$, $R^2$, $R^3$ and  are as defined hereinbefore).

Hydrolysis using an enzyme is known. For example, hydrolysis using an enzyme may be carried out in a mixture of a water-miscible organic solvent (ethanol, dimethylsulfoxide or mixed solvent thereof etc.) and water, in the presence or absence of buffer, using an ester cleaving enzyme (esterase, lipase etc.) at a temperature of from 0° C. to 50° C.

A compound of formula (II) may be prepared by subjecting to O-alkylation a compound of formula (III)

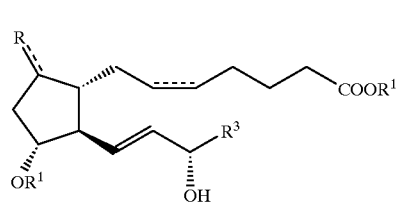

(wherein all symbols are as defined hereinbefore) and a compound of formula (IV)

$$R^2X \qquad (IV)$$

(wherein X is halogen atom, and $R^2$ is as defined hereinbefore).

O-alkylation is known. For example, O-alkylation may be carried out in an inert organic solvent (acetonitrile, tetrahydrofuran (THF), methylene chloride, benzene, acetone, or mixed solvent thereof etc.), in the presence of a catalyst (silver oxide, silver tetrafluoroborate, silver carbonate etc.) at a temperature of from 0° C. to 50° C.

A compound of formula (III) may be prepared by subjecting to hydrolysis under an acidic condition a compound of formula (V)

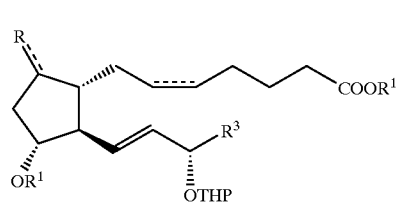

(wherein THP is 2-tetrahydropyranyl and the other symbols are as defined hereinbefore).

Hydrolysis under an acidic condition is known. For example, hydrolysis under an acidic condition may be carried out in a water-miscible organic solvent (methanol, ethanol, THF, dioxane or mixed solvent thereof etc.) using an aqueous solution of organic acid (acetic acid, p-toluenesulfonic acid, trichloroacetic acid, oxalic acid etc.) or inorganic acid (hydrochloric acid, sulfuric acid, hydrofluoric acid etc.), at a temperature of from 0° C. to 90° C.

A compound of formula (V) may be prepared by subjecting to O-alkylation a compound of formula (VI)

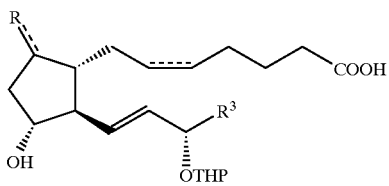
(VI)

wherein all symbols are as defined hereinbefore) and a compound of formula (VII)

R¹X        (VII)

(wherein X is halogen atom and R¹ is as defined hereinbefore).

O-Alkylation may be carried out as described hereinbefore.

(2) Among the compounds of formula (I), a compound wherein 5–6 position is double-bond and R ⋯⋯ is oxo; i.e. a compound of formula (Ic)

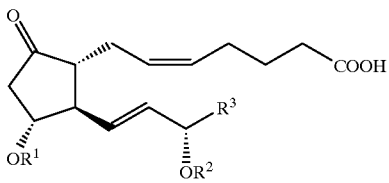
(Ic)

(wherein all symbols are as defined hereinbefore.) may be prepared by subjecting to oxidation reaction a compound of formula (XIV)

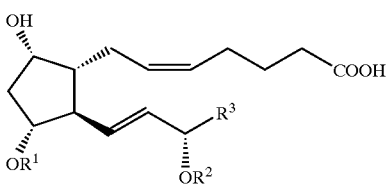
(XIV)

(wherein all symbols are as defined hereinbefore).

Oxidation reaction is known. For example, methods of Jones oxidation, chromic acid oxidation etc. are used.

A compound of formula (XIV) may be prepared by the following reaction scheme (A). In the reaction scheme, Ph is phenyl, Bu is butyl, DIBAL is diisobutyl aluminum hydride and the other symbols are as defined hereinbefore.

Reaction Scheme (A)

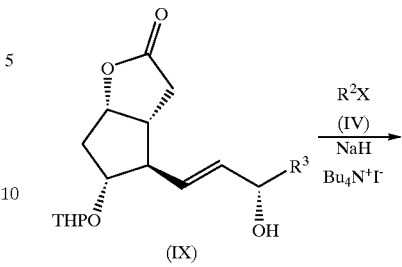
(IX)

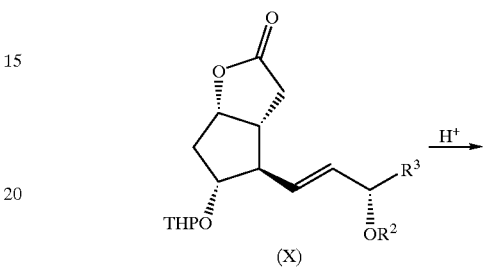
(X)

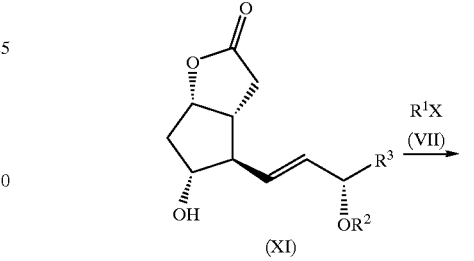
(XI)

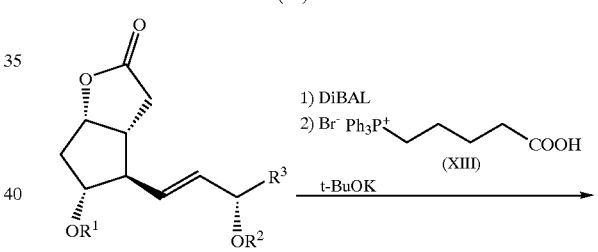
(XII)

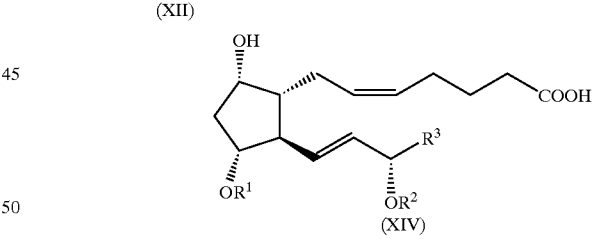
(XIV)

(3) Among the compounds of the present invention of formula (I), a compound wherein R² is the same group as R²; i.e. a compound of formula (Ia)

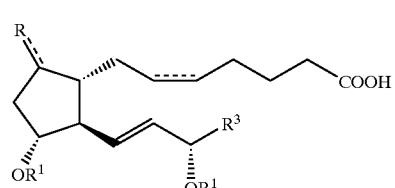
(Ia)

(wherein all symbols are as defined hereinbefore) may be prepared by subjecting to hydrolysis using an enzyme a compound of formula (VIII)

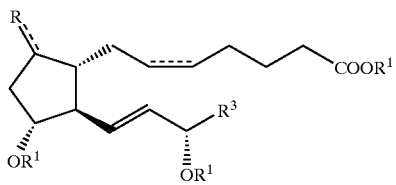

(VIII)

(wherein all symbols are as defined hereinbefore).

Hydrolysis using an enzyme may be carried out as described hereinbefore.

A compound of formula (VIII) may be prepared by subjecting to O-alkylation a compound of formula (IX)

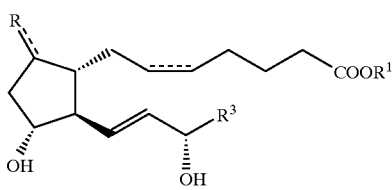

(IX)

(wherein all symbols are as defined hereinbefore) and a compound of formula (VII)

R¹X    (VII)

(wherein X is halogen atom and $R^1$ is as defined hereinbefore).

O-Alkylation may be carried out as described hereinbefore.

(4) Among the compounds of the present invention of formula (I), a compound wherein 5–6 position is double-bond, $R^2$ and $R^1$ are the same and R═ is oxo, i.e. a compound of formula (Ib)

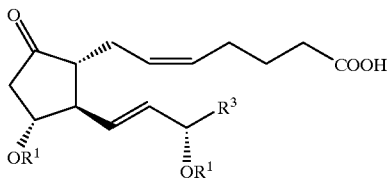

(Ib)

(wherein all symbols are as defined hereinbefore) may be prepared by subjecting to oxidation reaction a compound of formula (XVII)

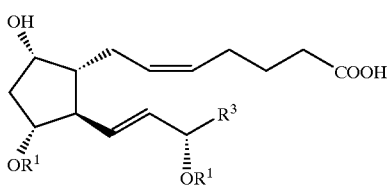

(XVII)

(wherein all symbols are as defined hereinbefore).

Oxidation reaction may be carried out as described hereinbefore.

A compound of formula (XVII) may be prepared by the following reaction scheme (B). In the reaction scheme, all symbols are as defined hereinbefore.

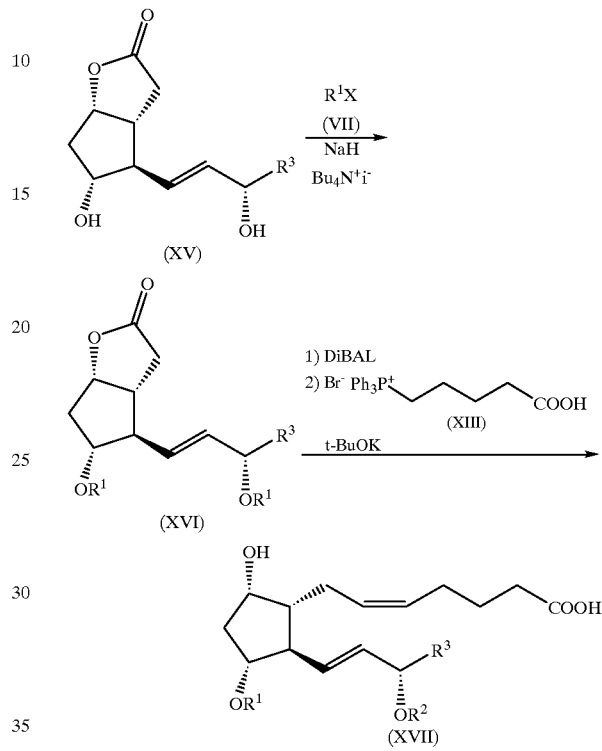

Reaction Scheme (B)

In each reaction of the present specification, reaction products may be purified by conventional techniques. For example, purification may be carried out by distillation under atmospheric or reduced pressure, by high performance liquid chromatography, thin layer chromatography or column chromatography using silica gel or magnesium silicate, by washing or by recrystallization etc. Purification may be carried out after each reaction, or after a series of reactions.

Starting Materials and Reagents

Starting materials and reagents used in the present invention are known per se or may be prepared by known methods. For example, among the compounds of formula (VI), prostaglandin $E_2$ derivatives wherein R═ is oxo and $R^3$ is n-pentyl are described in the specification of JP49-5946.

Pharmacological Activities

The compounds of the present invention of formula (I) bind strongly and act on $EP_3$ receptor which is $PGE_2$ receptor subtype.

For example, in the laboratory the effects of the compounds of the present invention were confirmed by binding assay using expression cell of prostanoids receptor subtype.
(i) Binding assay using expression cell of prostanoids receptor subtype The preparation of membrane fraction was carried out according to the method of Sugimoto et al. [J. Biol. Chem., 267, 6463–6466 (1992)], using expression CHO cell of the prostanoids receptor subtype (mouse $EP_1$, $EP_2$, $EP_{3\alpha}$, $EP_4$).

The standard assay mixture containing membrane fraction (0.5 mg/ml), and [3H]-PGE$_2$ in a final volume of 200 μl was incubated for 1 hour at room temperature. The reaction was terminated by addition of 3 ml of ice-cooled buffer. The mixture was filtered through a GF/B glass filter under reduced pressure. The radioactivity associated with the filter was measured by liquid scintillation counting.

Kd and Bmax values were determined from Scatchard plots [Ann. N.Y. Acad. Sci., 51, 660 (1949)]. Non-specific binding was calculated as the binding in the presence of an excess (2.5 μM) of unlabeled PGE$_2$. In the measurement of 3H-PGE$_2$ binding inhibitory activity, 2.5 nM of [3H]-PGE$_2$ and various concentrations of the compounds of the present invention were added. The following buffer was used in all reactions.

Buffer; 10 mM potassium phosphate (pH 6.0), 1 mM EDTA, 10 mM MgCl$_2$, 0.1 M NaCl.

The dissociation constant Ki (μM) of each compound was calculated by the following equation.

$$Ki=IC_{50}/(1+([C]/Kd))$$

The results are shown in the Table.

| | Dissociation Constant Ki (μM) | | | |
|---|---|---|---|---|
| Ex. No. | EP$_1$ | EP$_2$ | EP$_{3\alpha}$ | EP$_4$ |
| 1 | >10 | 2.4 | 0.0036 | 4.2 |
| 1(a) | >10 | 1.1 | 0.0063 | 1.3 |
| 1(b) | 0.97 | 0.53 | 0.0027 | 2.5 |
| 1(e) | 2.4 | 1.3 | 0.0061 | 3.7 |
| 1(f) | 0.31 | >10 | 0.0029 | >10 |
| 1(h) | 0.039 | 0.034 | 0.0017 | 0.073 |
| 2 | >10 | 0.6 | 0.04 | 5.9 |

Toxicity

The toxicity of the compounds of the present invention is very low and therefore, it is confirmed that these compounds are safe for pharmaceutical use.

Application to Pharmaceuticals

The compounds of the present invention of formula (I) bind selectively and act on PGE$_2$ receptor, especially on EP$_3$ subtype receptor and therefore are useful for prevention and/or treatment of liver diseases, kidney diseases, pancreatitis, myocardial infarction etc.

For the purpose described hereinbefore, the compounds of formula (I), non-toxic salts thereof, CD clathrates thereof may normally be administered systemically or locally, by oral or parenteral administration.

The doses to be administered are determined depending upon age, body weight, symptom, the desired therapeutic effect, the route of administration, and the duration of the treatment etc. In the human adult, the doses per person per dose are generally from 1 μg to 100 mg, by oral administration, from once up to several times per day, and from 0.1 μg to 10 mg, by parenteral administration (preferably intravenously) from once up to several times per day, or by continuous administration for from 1 hour to 24 hours per day into vein.

As mentioned hereinbefore, the doses to be administered depend upon various conditions. Therefore, there are cases in which doses lower than or greater than the ranges specified hereinbefore may be used.

The compounds of the present invention may be administered in the form, for example, of solid compositions, liquid compositions or other compositions for oral administration, or injections, liniments or suppositories etc. for parenteral administration.

Solid compositions for oral administration include compressed tablets, pills, capsules, dispersible powders, and granules etc.

Capsules include hard capsules and soft capsules.

In these solid compositions, one or more of the active compound(s) are admixed with at least one inert diluent, e.g. lactose, mannitol, mannit, glucose, hydroxypropyl cellulose, microcrystalline cellulose, starch, polyvinyl pyrrolidone, magnesium metasilicate aluminate. The composition may contain, according to the conventional manner, additives other than inert diluents, e.g. lubricating agents such as magnesium stearate, disintegrating agents such as cellulose calcium glycolate, agents to assist dissolution such as glutamic acid, aspartic acid. The tablets or pills may, if desired, be coated with film of gastric or enteric material such as sugar, gelatin, hydroxypropyl cellulose, hydroxypropyl cellulose phthalate etc. or be coated with more than one film. Coating may include containment within capsules of absorbable materials such as gelatin.

Liquid compositions for oral administration include pharmaceutically acceptable emulsions, solutions, syrups and elixirs etc. In such liquid compositions, one or more of the active compound(s) may be contained in inert diluent(s) commonly used in the art (e.g. purified water, ethanol). Besides inert diluents, such compositions may also comprise assisting agents (e.g. wetting agents, suspending agents), sweetening agents, flavoring agents, perfuming agents and preserving agents.

Other compositions for oral administration include spray compositions which contain one or more of the active compound(s), prepared by methods known per se. Spray compositions may comprise stabilizing agents such as sodium sulfite hydride, isotonic buffers such as sodium chloride, sodium citrate or citric acid. For the preparation of such spray compositions, for example, the method described in the U.S. Pat. No. 2,868,691 or U.S. Pat. No. 3,095,355 may be used.

Injections for parenteral administration include sterile aqueous or non-aqueous solutions, suspensions and emulsions. Aqueous solutions and suspensions include, for example, distilled water for injection and physiological salt solution. Non-aqueous solution and suspensions include, for example, propylene glycol, polyethylene glycol, vegetable oil such as olive oil, alcohol such as ethanol, POLYSORBATE80 (registered trademark) etc. These compositions may comprise assisting agents such as preserving agents, wetting agents, emulsifying agents, dispersing agents, stabilizing agents, agents assisting dissolution (e.g. glutamic acid, aspartic acid etc.). They may be sterilized for example, by filtration through a bacteria-retaining filter, by incorporation of sterilizing agents in the compositions or by irradiation. They may also be manufactured in the form of sterile solid compositions which may be dissolved in sterile water or some other sterile solvent(s) for injection before use.

Other compositions for parenteral administration include liquids for external use, and ointment, endermic liniments, suppositories for rectal administration and pessaries for vaginal administration etc. which comprise one or more of active compound(s) and may be prepared by conventional methods.

Best Mode for Carrying Out the Invention

The following reference examples and examples are intended to illustrate, but do not limit, the present invention. The solvents in parentheses show the developing or eluting solvents and the ratios of the solvents used are by volume in chromatographic separations. Unless otherwise specified, NMR is measured using deuterated chloroform.

REFERENCE EXAMPLE 1

11α,15α-Dimethoxy-9-oxoprosta-5Z,13E-dienoic acid methyl ester

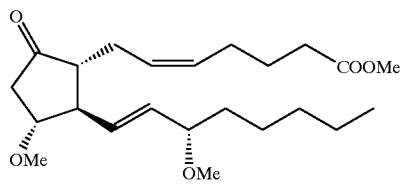

Under atmosphere of argon, to an ice-cooled solution of PGE₂ (900 mg) in acetonitrile (20 ml) were added silver oxide (2.36 g) and methyl iodide (640 μl) and the mixture was stirred at room temperature. After stirring for 13 hours and 21 hours, to the mixture were added silver oxide (1.00 g) and methyl iodide (640 μl), respectively, and the mixture was stirred for 37 hours in total. The reaction solution was filtered, and the filtrate was purified by column chromatography on silica gel (hexane-ethyl acetate) to give the title compound (812 mg) having the following physical data.

TLC: Rf 0.67 (hexane:ethyl acetate=1:1).

EXAMPLE 1

11α,15α-Dimethoxy-9-oxoprosta-5Z,13E-dienoic acid

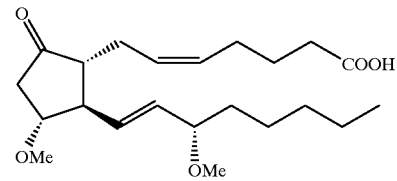

To a solution of 11α,15α-dimethoxy-9-oxoprosta-5Z, 13E-dienoic acid methyl ester (prepared in Reference Example 1, 500 mg) in ethanol (5 ml) was added phosphoric acid buffer (50 ml, pH 7.4) followed by adding porcine liver esterase (1 ml), and the mixture was stirred for 30 hours. After the reaction, the reaction mixture was cooled with ice, and thereto was added 1N hydrochloric acid till it became pH 4. The reaction solution was extracted with ethyl acetate. The organic layer was washed, dried and concentrated under reduced pressure. The residue was purified by column chromatography on silica gel (hexane-ethyl acetate-acetic acid) to give the title compound (311 mg) having the following physical data.

TLC: Rf 0.19 (hexane:ethyl acetate=2:1, 1% acetic acid);
NMR: δ 5.66 (1H, dd, J=16, 7.5 Hz), 5.44 (1H, dd, J=16, 7.2 Hz), 5.40 (2H, m), 3.72 (1H, m), 3.57 (1H, m), 3.38 (3H, s), 3.29 (3H, s), 2.77 (1H, ddd, J=19, 7.1, 1.0 Hz), 2.58 (1H, dt, J=11, 7.9 Hz), 2.34 (2H, t, J=7.4 Hz), 2.50–2.00 (6H, m), 1.78–1.08 (10H, m), 0.89 (3H, t, J=6.5 Hz).

EXAMPLE 1(a)~1(h)

By the same procedure described in reference example 1 and example 1, the title compounds having the following physical data were obtained.

EXAMPLE 1(a)

11α,15α-Dimethoxy-9-oxoprosta-13E-enoic acid

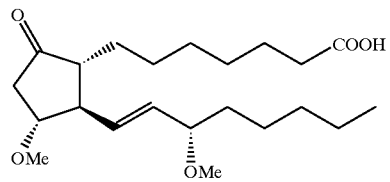

TLC: Rf 0.20 (hexane:ethyl acetate=2:1 ,1% acetic acid);
NMR (CDCl₃): δ 5.65 (1H, dd, J=16, 7.6 Hz, olefin), 5.45 (1H, dd, J=16, 7.4 Hz, olefin), 3.71 (1H, m), 3.55 (1H, m), 3.38 (3H, s, OMe), 3.28 (3H, s, OMe), 2.76 (1H, dd, J=19, 7.0 Hz), 2.54 (1H, dt, J=11, 7.8 Hz), 2.33 (2H, t, J=7.3 Hz), 2.18 (1H, dd, J=19, 8.4 Hz), 2.00 (1H, m), 1.80–1.15 (18H, m), 0.88 (3H, t, J=6.4 Hz EXAMPLE 1(b)

11α,15α-Dimethoxy-9-oxo-16,16-dimethylprosta-5Z,13E-dienoic acid

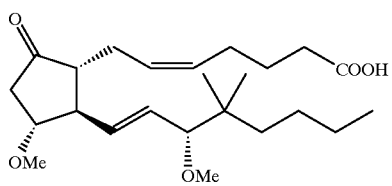

TLC: Rf 0.40 (ethyl acetate:hexane=1:1);
NMR (CDCl₃): δ 5.62 (1H, dd, J=16, 7 Hz), 5.57–5.20 (3H, m), 3.70 (1H, m), 3.38 (3H, s), 3.26 (3H, s), 3.20 (1H, m), 2.77 (1 H, dd, J=20, 7 Hz), 2.61 (1H, dt, J=11, 8 Hz), 2.52–2.00 (8H, m), 1.70 (2H, m), 1.40–1.06 (6H, m), 1.00–0.77 9H, m).

EXAMPLE 1(c)

11α,15α-Dimethoxy-9-oxo-17α-methylprosta-5Z,13E-dienoic acid

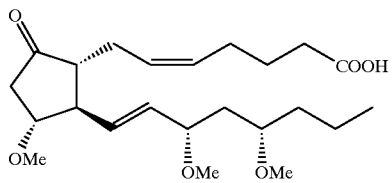

TLC: Rf 0.36 (ethyl acetate:hexane=1:1);
NMR (CDCl₃): δ 5.61 (1H, dd, J=15, 8 Hz), 5.50–5.33 (3H, m), 3.75–3.63 (2H, m), 3.36 (3H, s), 3.30 (3H, s), 2.77 (1H, ddd, J=19, 7,2 Hz), 2.56 (1H, dt, J=12, 8 Hz), 2.45–2.25 (4H, m), 2.18–2.04 (4H, m), 1.74–1.60 (4H, m), 1.40–1.17 (4H, m), 1.16–1.06 (1H, m), 0.92–0.84 (6H, m).

EXAMPLE 1(d)

11α,15α-Dimethoxy-9-oxo-20-norprosta-5Z 13E-dienoic acid

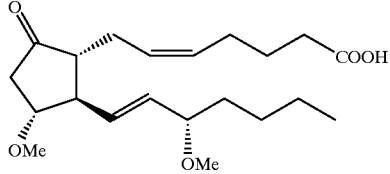

TLC: Rf 0.14 (ethyl acetate:hexane=1:1);

NMR (CDCl3): δ 5.66 (1H, dd, J=16, 8 Hz), 5.50–5.36 (3H, m), 3.71 (1H, m), 3.57 (1H, q, J=7 Hz), 3.38 (3H, s), 3.30 (3H, s), 2.77 (1H, ddd, J=19, 7, 1 Hz), 2.58 (1H, dt, J=12, 8 Hz), 2.40 (1H, dt, J=14, 8 Hz), 2.36–2.26 (3H, m), 2.20–2.02 (4H, m), 1.78–1.56 (3H, m), 1.52–1.42 (1H, m), 1.38–1.22 (4H, m), 0.90 3 H, t, J=7 Hz).

EXAMPLE 1(e)

11α,15α-Dimethoxy-9-oxo-20-methylprosta-5Z,13E-dienoic acid

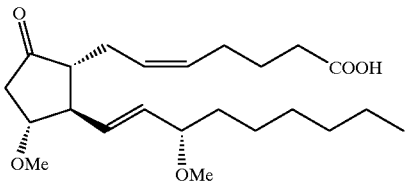

TLC: Rf 0.17 (ethyl acetate:hexane 32 1:1);

NMR (CDCl$_3$): δ 5.67 (1H, dd, J=16, 8 Hz), 5.50–5.36 (3H, m), 3.71 (1H, m), 3.59 (1H, m), 3.38 (3H, s), 3.30 (3H, s), 2.77 (1H, ddd, J=18, 7, 1 Hz), 2.57 (1H, dt, J=12, 8 Hz), 2.40 (1H, dt, J=15, 5 Hz), 2.36–2.25 (2H, m), 2.22–2.02 (4H, m), 1.80–1.56 (4H, m), 1.52–1.43 (1H, m), 1.40–1.22 (8H, m), 0.88 (3H, t, J=7 Hz).

EXAMPLE 1(f)

11α,15α-Dimethoxy-9-oxo-16-phenoxy-17,18,19,20-tetranorprosta-5Z,13E-dienoic acid

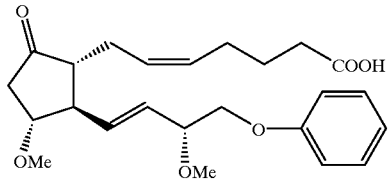

TLC: Rf 0.17 (hexane:ethyl acetate=1:1);

NMR (CDCl$_3$): δ 7.32–7.24 (2H, m), 6.97–6.85 (3H, m), 5.85 (1H, dd, J=15.4, 7.4 Hz), 5.62 (1H, dd, J=15.4, 6.2 Hz), 5.45–5.28 (2H, m), 4.10–3.92 (3H, m), 3.80–3.68 (1H, m), 3.42 (3H, s), 3.39 (3H, s), 2.78 (1H, ddd, J=18.8, 7.4, 1.2 Hz), 2.69–2.55 (1H, m), 2.47–1.99 (6H, m), 2.27 (2H, t, J=6.8 Hz), 1.70–1.55 (2H, m).

EXAMPLE 1(g)

11α,15α-Dimethoxy-9-oxo-17-phenyl-18,19,20-trinorprosta-5Z,13E-dienoic acid

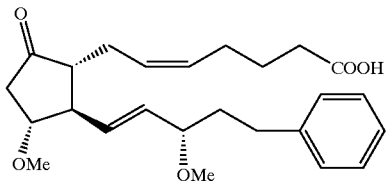

TLC: Rf 0.33 (hexane:ethyl acetate =1:1);

NMR (CDCl$_3$): δ 7.34–7.12 (5H, m), 5.67 (1H, dd, J=15.8, 7.4 Hz), 5.50 (1H, dd, J=15.8, 7.4 Hz), 5.50–5.30 (2H, m), 3.71 (1 H, td, J=8.2, 7.0 Hz), 3.63–3.53 (1H, m), 3.38 (3H, s), 3.31 (3H, s), 2.83–1.60 (16H, m).

EXAMPLE 1(h)

11α,15α-Dimethoxy-9β-chloroprosta-5Z,13E-dienoic acid

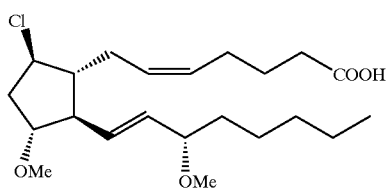

TLC: Rf 0.26 (hexane:ethyl acetate=2:1);

NMR (CDCl$_3$): δ 5.61 (1H, dd, J=15.4, 8.0 Hz), 5.50–5.32 (3H, m), 3.98 (1H, q, J=7.8 Hz), 3.71–3.63 (1H, m), 3.58–3.48 (1H, m), 3.31 (3H, s), 3.27 (3H, s) 2.36 (2H, t, J=6.9 Hz), 2.30–1.20 (18H, m), 0.88 (3H, t, J=6.4 Hz).

REFERENCE EXAMPLE 2

(E)-2-Oxa-6-syn-(3α-ethoxy-1-octenyl)-7-anti-ethoxy-cis-bicyclo[3.3.0]octan-3-one

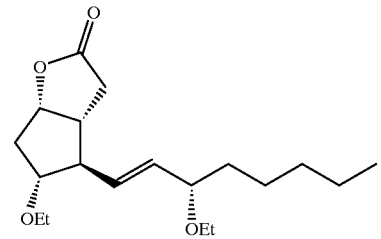

Under atmosphere of argon, to a solution of (E)-2-oxa-6-syn-(3α-hydroxy-1-octenyl)-7-anti-hydroxy-cis-bicyclo [3.3.0]octan-3-one (80 mg) in anhydrous DMF (1 ml) were added sodium hydride (26 mg), tetrabutylammonium iodide (11 mg) and ethyl iodide (60 μl), and the mixture was stirred at room temperature for 30 minutes and at 60° C. for 1 hour. The reaction mixture was cooled to 0° C., and thereto was added a saturated aqueous solution of ammonium chloride. The reaction mixture was extracted with ethyl acetate, and the organic layer was washed, dried and concentrated under reduced pressure. The residue was purified by column chromatography on silica gel (hexane-ethyl acetate) to give the title compound having the following physical data.

TLC: Rf 0.43 (hexane:ethyl acetate=2:1).

REFERENCE EXAMPLE 3

11α,15α-Diethoxy-9α-hydroxy-prosta-5Z,13E-dienoic acid

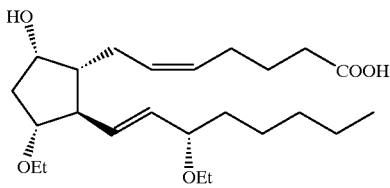

Under atmosphere of argon, a solution of (E)-2-oxa-6-syn-(3α-ethoxy-1 -octenyl) -7-anti-2α-ethoxy-cis-bicyclo [3.3.0]octan-3-one (35 mg) in anhydrous toluene (0.5 ml) was cooled to −78° C., and thereto was added diisobutyl aluminum hydride (1.01 M, 130 μl) dropwise, and the mixture was stirred for 30 minutes, and stirred at 0° C. for 20 minutes. To the reaction mixture was added a saturated aqueous solution of ammonium chloride. The reaction mixture was extracted with ethyl acetate. The organic layer was washed, dried and concentrated under reduced pressure. The residue was used in the next reaction without further purification.

Under atmosphere of argon, a solution of 4-carboxybutyltriphenyl phosphonium bromide (144 mg) and potassium t-butoxide (73 mg) in anhydrous toluene (1.5 ml) was stirred at 80° C. for 30 minutes. The reaction mixture was cooled to 0° C., and thereto was added dropwise a solution of the aldehyde obtained in the above reaction in anhydrous toluene (0.5 ml) and the mixture was stirred at room temperature for 30 minutes. The reaction mixture was cooled to 0° C., and acidified by adding a saturated aqueous solution of oxalic acid and the mixture was extracted with ethyl acetate. The organic layer was washed, dried, and purified by column chromatography on silica gel (hexane-ethyl acetate) to give the title compound having the following physical data.

TLC: Rf 0.44 (chloroform: methanol=1:1).

EXAMPLE 2

11α,15α-Diethoxy-9-oxoprosta-5Z,13E -dienoic acid

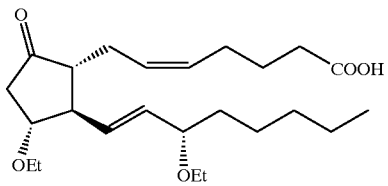

To a solution of 11α,15α-diethoxy-9α-hydroxy-prosta-5Z,13E-dienoic acid (30 mg, prepared in reference example 3) in acetone (0.7 ml) which was cooled to −30° C., was added Jones reagent and the mixture was stirred for 10 minutes. To the reaction solution were added isopropanol, water, ethyl acetate successively, and the mixture was warmed to 0° C. The reaction mixture was extracted with ethyl acetate, and the organic layer was washed, dried and purified by column chromatography on silica gel (hexane-ethyl acetate-acetic acid) to give the title compound having the following physical data.

TLC: Rf 0.33 (chloroform:methanol=19:1);

NMR: δ 8.60(1H, br), 5.59 (1H, dd, J=16, 7.1 Hz), 5.49 (1H, dd, J=16, 6.9 Hz), 5.38 (2H, m), 3.67 (5H, m), 3.34 (1H, m), 2.75 (1H, ddd, J=18, 7.0, 1.2 Hz), 2.58 (1H, dt, J=11, 7.7 Hz), 2.47–1.96 (8H, m), 1.79–1.24 (10H, m), 1.19 (3H, t, J=7.0 Hz), 1.18 (3H, t, J=7.0 Hz), 0.88 (3H, t, J=6.6 Hz).

Formulation Example

The following components were admixed in a conventional method, dried, added microcrystalline cellulose to weigh 10 g in total, mixed until homogeneous and punched out in a conventional method to obtain 100 tablets each containing 30 μg of active ingredient.

| A solution of 11α, 15α-dimethoxy-9-oxoprosta-5Z, 13E-dienoic acid | | |
|---|---|---|
| (3 mg) in ethanol | 10 | ml |
| Magnesium stearate | 100 | mg |
| Silicon dioxide | 20 | mg |
| Talc | 10 | mg |
| Carboxymethylcellulose calcium | 200 | mg |
| Microcrystalline cellulose | 5.0 | g |

What is claimed is:

1. An 11,15-O-dialkyl prostaglandin E derivative of formula (I)

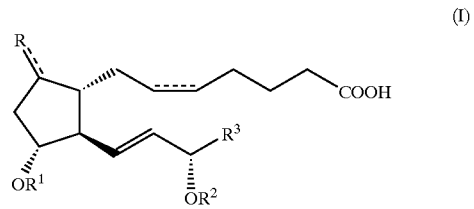

(wherein R is oxo or halogen atom, $R^1$ and $R^2$ are each independently C1–4 alkyl, $R^3$ is C1–10 alkyl, C2–10 alkenyl, C2–10 alkenyl, or C1–10 alkyl, C2–10 alkenyl or C2–10 alkynyl substituted by phenyl, phenoxy, C3–7 cycloalkyl or C3–7 cycloalkyloxy, wherein phenyl and cycloalkyl may be substituted by 1–3 of C1–4 alkyl, C1–4 alkoxy, halogen, trihalomethyl or nitro, and ═══ is bond or double-bond, or a non-toxic salts thereof or cyclodextrin clathrates thereof.

2. A compound according to claim 1, which is 11α,15α-dimethoxy-9-oxoprosta-5Z,13E-dienoic acid.

3. A compound according to claim 1, which is 11α,15α-diethoxy-9oxoprosta-5Z,13E-dienoic acid.

4. A compound according to claim 1, which is 11α,15α-dimethoxy-9-oxoprost-13E-enoic acid.

5. A compound according to claim 1, which is 11α,15α-dimethoxy-9-oxo-16,16-dimethylprost-5Z,13E-dienoic acid.

6. A compound according to claim 1, which is 11α,15α-dimethoxy-9-oxo17 α-methylprost-5Z,13E-dienoic acid.

7. A compound according to claim 1, which is 11α,15α-dimethoxy-9-oxo-20-norprost-5Z,13E-dienoic acid.

8. A compound according to claim 1, which is 11α,15α-dimethoxy-9-oxo-20-methylprost-5Z,13E-dienoic acid.

9. A compound according to claim 1, which is 11α,15α-dimethoxy-9-oxo-16-phenoxy-17,18,19,20-tetranorprost-5Z,13E-dienoic acid.

10. A compound according to claim 1, which is 11α,15α-dimethoxy-9-oxo-17-phenyl-18,19,20-trinorprost-5Z,13E-dienoic acid.

11. A compound according to claim 1, which is 11α,15α-dimethoxy-9β-chloroprost-5Z,13E-dienoic acid.

12. A process for the preparation of a compound of formula (I)

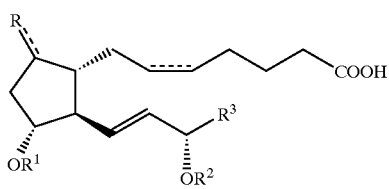

(I)

(wherein R is oxo or halogen atom, $R^1$ and $R^2$ are each independently C1–4 alkyl, $R^3$ is C1–10 alkyl, C2–10 alkenyl, C2–10 alkynyl, or C1–10 alkyl, C2–10 alkenyl or C2–10 alkynyl substituted by phenyl, phenoxy, C3–7 cycloalkyl or C3–7 cycloalkyloxy, wherein phenyl and cycloalkyl may be substituted by 1–3 of C1–4 alkyl, C1–4 alkoxy, halogen, trihalomethyl or nitro, and ═══ is bond or double-bond characterized by subjecting to hydrolysis using an enzyme a compound of formula (II)

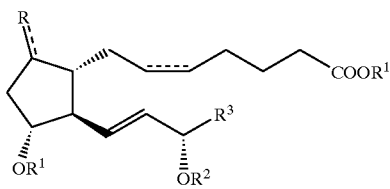

(II)

(wherein all symbols are as defined herein).

13. A process for the preparation of a compound of formula (Ic)

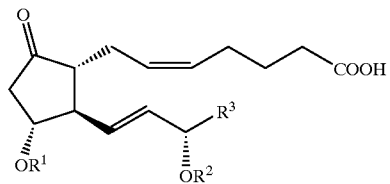

(Ic)

(wherein $R^1$, $R^2$ and $R^3$ are as defined in claim 1) characterized by subjecting to oxidation reaction a compound of formula (XIV)

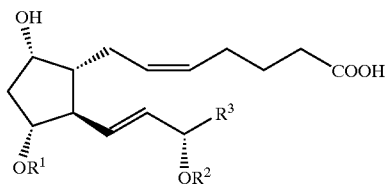

(XIV)

(wherein all symbols are as defined herein).

14. A pharmaceutical agent which contains an 11,15-O-dialkyl prostaglandin E derivatives of formula (I) described in claim 1 or a non-toxic salts thereof as active ingredient and a carrier.

* * * * *